(12) United States Patent
Pedersen et al.

(10) Patent No.: US 12,337,276 B2
(45) Date of Patent: Jun. 24, 2025

(54) DEVICE AND A MEMBRANE PROCESS FOR SEPARATING GAS COMPONENTS FROM A GAS STREAM HAVING VARYING COMPOSITION OR FLOW RATE

(71) Applicant: EVONIK OPERATIONS GMBH, Essen (DE)

(72) Inventors: Steven Kristian Pedersen, Nottawa (CA); Hendrik Derk Hoving, Mountain lakes, NJ (US); Markus Priske, Salzburg (AT); Kah Peng Lee, Seewalchen (AT); Norbert Krutzler, Pühret (AT)

(73) Assignee: Evonik Operations GmbH, Essen (DE)

( * ) Notice: Subject to any disclaimer, the term of this patent is extended or adjusted under 35 U.S.C. 154(b) by 720 days.

(21) Appl. No.: 17/427,555

(22) PCT Filed: Jan. 22, 2020

(86) PCT No.: PCT/EP2020/051497
§ 371 (c)(1),
(2) Date: Jul. 30, 2021

(87) PCT Pub. No.: WO2020/156902
PCT Pub. Date: Aug. 6, 2020

(65) Prior Publication Data
US 2022/0134274 A1    May 5, 2022

Related U.S. Application Data

(60) Provisional application No. 62/800,168, filed on Feb. 1, 2019.

(51) Int. Cl.
*C07C 7/144* (2006.01)
*B01D 53/22* (2006.01)
(Continued)

(52) U.S. Cl.
CPC ......... *B01D 53/226* (2013.01); *B01D 53/227* (2013.01); *B01D 53/26* (2013.01);
(Continued)

(58) Field of Classification Search
None
See application file for complete search history.

(56) References Cited

U.S. PATENT DOCUMENTS

| 5,053,058 A | 10/1991 | Mitariten |
| 5,727,903 A | 3/1998 | Borray et al. |

(Continued)

FOREIGN PATENT DOCUMENTS

| CN | 205420305 U | 8/2016 |
| EP | 1 585 181 | 10/2005 |

(Continued)

OTHER PUBLICATIONS

U.S. Appl. No. 15/748,183, filed Jan. 28, 2018, US-2018/0221824 A1, Aug. 9, 2018, Visser.

(Continued)

*Primary Examiner* — Tam M Nguyen
(74) *Attorney, Agent, or Firm* — Law Office of: Michael A, Sanzo, LLC

(57) ABSTRACT

A device for separating a gas stream which has a compressor and three membrane separation units in series, connected to pass the retentate stream of each of the first two units to the subsequent membrane separation unit, comprises conduits for recycling the permeate streams of the second and the third membrane separation unit to upstream of the compressor and a control device controlling the fraction of the second permeate stream which is recycled. Adjusting which fraction of the second permeate is recycled can be used to maintain a target composition of the retentate obtained in the (Continued)

third membrane separation unit when the flow rate or the composition of the gas stream changes.

7 Claims, 2 Drawing Sheets

(51) Int. Cl.
    *B01D 53/26*     (2006.01)
    *C10L 3/10*     (2006.01)

(52) U.S. Cl.
    CPC ............. *C07C 7/144* (2013.01); *C10L 3/104* (2013.01); *C10L 2290/10* (2013.01); *C10L 2290/548* (2013.01)

(56) References Cited

U.S. PATENT DOCUMENTS

| | | | |
|---|---|---|---|
| 6,197,090 | B1 | 3/2001 | Yamashita et al. |
| 6,572,678 | B1 | 6/2003 | Wijmans et al. |
| 8,568,512 | B2 | 10/2013 | Siegel et al. |
| 8,748,643 | B2 | 6/2014 | Priske et al. |
| 8,821,614 | B1 * | 9/2014 | Albenze ............. G01N 15/0826 95/12 |
| 8,969,628 | B2 | 3/2015 | Priske et al. |
| 8,999,036 | B2 | 4/2015 | Pierce |
| 8,999,038 | B2 | 4/2015 | Ungerank et al. |
| 9,005,335 | B2 | 4/2015 | Baker et al. |
| 9,314,735 | B2 | 4/2016 | Balster et al. |
| 9,353,040 | B2 | 5/2016 | Baumgarten et al. |
| 9,393,537 | B2 | 7/2016 | Hamers et al. |
| 9,428,433 | B2 | 8/2016 | Fridag et al. |
| 9,469,048 | B2 | 10/2016 | Ungerank et al. |
| 9,624,153 | B2 | 4/2017 | Becker et al. |
| 9,643,153 | B2 | 5/2017 | Meier et al. |
| 9,676,805 | B2 | 6/2017 | Dyballa et al. |
| 9,713,791 | B2 | 7/2017 | Priske et al. |
| 9,770,687 | B2 | 9/2017 | Ungerank et al. |
| 9,873,093 | B2 | 1/2018 | Visser et al. |
| 9,988,326 | B2 | 6/2018 | Paget et al. |
| 10,017,443 | B2 | 7/2018 | Leuken et al. |
| 10,040,036 | B2 | 8/2018 | Ungerank et al. |
| 10,118,136 | B2 | 11/2018 | Ungerank et al. |
| 10,456,750 | B2 | 10/2019 | Visser et al. |
| 10,471,380 | B2 | 11/2019 | Priske |
| 10,792,619 | B2 | 10/2020 | Lim et al. |
| 10,905,995 | B2 | 2/2021 | Prince et al. |
| 10,933,378 | B2 | 3/2021 | Visser et al. |
| 11,498,026 | B2 | 11/2022 | Wu et al. |
| 11,857,916 | B2 | 1/2024 | Winkler et al. |
| 2007/0113736 | A1 | 5/2007 | Bandosz |
| 2007/0125537 | A1 | 6/2007 | Lokhandwala et al. |
| 2010/0288701 | A1 | 11/2010 | Zhou et al. |
| 2012/0000355 | A1 | 1/2012 | Sharma et al. |
| 2014/0137735 | A1 | 5/2014 | Bhandari et al. |
| 2014/0241968 | A1 | 8/2014 | Wennergren et al. |
| 2015/0336046 | A1 | 11/2015 | Ungerank et al. |
| 2016/0082393 | A1 | 3/2016 | Priske et al. |
| 2016/0317981 | A1 | 11/2016 | Ungerank et al. |
| 2017/0320009 | A1 | 11/2017 | Hirata et al. |
| 2018/0099251 | A1 | 4/2018 | Visser et al. |
| 2018/0221824 | A1 | 8/2018 | Visser et al. |
| 2019/0001263 | A1 | 1/2019 | Prince et al. |
| 2020/0047113 | A1 | 2/2020 | Chareyre et al. |
| 2020/0254383 | A1 | 8/2020 | Roodbeen |
| 2020/0269188 | A1 | 8/2020 | Hasegawa et al. |
| 2020/0316516 | A1 | 10/2020 | Wu et al. |
| 2021/0339189 | A1 | 11/2021 | Winkler et al. |
| 2021/0363463 | A1 | 11/2021 | Xie et al. |
| 2021/0394125 | A1 | 12/2021 | Peters et al. |
| 2023/0271130 | A1 | 8/2023 | Priske et al. |

FOREIGN PATENT DOCUMENTS

| | | | | |
|---|---|---|---|---|
| EP | 1921443 | A1 * | 5/2008 | ............. G01N 25/18 |
| EP | 3454059 | A1 * | 3/2019 | ........... G01N 29/024 |
| GB | 2 010 794 | | 7/1979 | |
| GB | 2534383 | | 7/2016 | |
| JP | 2018086620 | | 6/2018 | |
| KR | 10-1840337 | | 3/2018 | |
| KR | 10-1840340 | | 3/2018 | |
| KR | 10-1840343 | | 3/2018 | |
| KR | 10-1863058 | | 6/2018 | |
| WO | WO 2014/183977 | | 11/2014 | |
| WO | WO 2015/017875 | | 2/2015 | |
| WO | WO 2015/177009 | | 11/2015 | |
| WO | WO 2016/198450 | | 12/2016 | |
| WO | WO 2019/165597 | | 6/2019 | |
| WO | WO 2022/012944 | | 1/2022 | |
| WO | WO 2023/011919 | | 9/2023 | |

OTHER PUBLICATIONS

U.S. Appl. No. 16/305,575, filed Nov. 29, 2018, US-2020/0316516 A1, Oct. 8, 2020, Wu.
International Search Report for PCT/EP2021/068142 filed Jul. 1, 2021, corresponding to copending U.S. Appl. No. 18/015,866.
Written Opinion of the International Searching Authority for PCT/EP2021/068142 filed Jul. 1, 2021, corresponding to copending U.S. Appl. No. 18/015,866.
International Preliminary Report on Patentability for PCT/EP2021/068142 filed Jul. 1, 2021, corresponding to copending U.S. Appl. No. 18/015,866.
European Search Report and Search Opinion for EP 20185597 filed Jul. 14, 2020, corresponding to copending U.S. Appl. No. 18/015,866.
Chen, et al., "Membrane gas separation technologies for biogas upgrading," *RSC Advances* 5(31):24399-24448 (Jan. 2015).
Falbo, et al., "Polyimide hollow fiber membranes for $CO_2$ separation from wet gas mixtures," *Brazilian Journal of Chemical Engineering* 31(4):1023-1034 (Dec. 2014).
Scholz, et al., "Modeling Gas Permeation by Linking Nonideal Effects," *Ind. Eng. Chem. Res.* 52(3):1079-1088 (Jan. 2013).
Shin, et al., "Biogas separation using a membrane gas separator: Focus on $CO_2$ upgrading without $CH_4$ loss," *Process Safety and Environmental Protection* 129:348-358 (Jul. 2019).
Non Final Office Action for copending U.S. Appl. No. 17/281,962, mailed Mar. 13, 2023.
U.S. Appl. No. 18/015,866, filed Jan. 12, 2023, Priske.
International Search Report for international application PCT/EP2019/075001 filed Sep. 18, 2019; corresponding to copending application U.S. Appl. No. 17/281,962.
Written Opinion of the International Searching Authority for international application PCT/EP2019/075001 filed Sep. 18, 2019; corresponding to copending application U.S. Appl. No. 17/281,962.
International Preliminary Report on Patentability for international application PCT/EP2019/075001 filed Sep. 18, 2019; corresponding to copending application U.S. Appl. No. 17/281,962.
European Search Report European application EP 18 19 8221, filed Oct. 2, 2018; corresponding to copending application U.S. Appl. No. 17/281,962.
Alqaheem, et al., "Polymeric Gas-Separation Membranes for Petroleum Refining," *International Journal of Polymer Science* 2017:1-19 (Jan. 2017).
Castrillon, et al., "$CO_2$ and $H_2S$ Removal from $CH_4$-Rich Streams by Adsorption on Activated Carbons Modified with $K_2CO_3$, NaOH, or $Fe_2O_3$," *Energy & Fuels* 30(11):9596-9604 (Oct. 2016).
Chiang, et al., "Effect of Relative Humidity on Adsorption Breakthrough of $CO_2$ on Activated Carbon Fibers," *Materials* 10(11):1-14 (Nov. 2017).
Leuch, et al., "Hydrogen Sulfide Adsorption and Oxidation onto Activated Carbon Cloths: Applications to Odorous Gaseous Emission Treatments," *Langmuir* 19(26):10869-10877 (Dec. 2003).
Yin, et al., "Effects of temperature and relative humidity on the methane permeability rate of biogas storage membranes," *International Journal of Green Energy* 13(9):951-956 (Jul. 2016).

(56) References Cited

OTHER PUBLICATIONS

U.S. Appl. No. 17/281,962, filed Mar. 31, 2021, Winkler.
International Search Report for international application PCT/EP2022/070296 filed Jul. 20, 2022; corresponding to copending application U.S. Appl. No. 18/293,448.
Written Opinion of the International Searching Authority for international application PCT/EP2022/070296 filed Jul. 20, 2022; corresponding to copending application U.S. Appl. No. 18/293,448.
International Preliminary Report on Patentability for international application PCT/EP2022/070296 filed Jul. 20, 2022; corresponding to copending application U.S. Appl. No. 18/293,448.
U.S. Appl. No. 18/293,448, filed Jan. 30, 2024, Priske.
International Search Report for corresponding international application PCT/EP2020/051497, filed Jan. 22, 2020.
Written Opinion of the International Searching Authority for corresponding international application PCT/EP2020/051497, filed Jan. 22, 2020.
International Preliminary Report on Patentability for corresponding international application PCT/EP2020/051497, filed Jan. 22, 2020.
U.S. Appl. No. 17/348,747, filed Jun. 15, 2021, US-2021/0394125 A1, Dec. 23, 2021, Peters.

* cited by examiner

DEVICE AND A MEMBRANE PROCESS FOR SEPARATING GAS COMPONENTS FROM A GAS STREAM HAVING VARYING COMPOSITION OR FLOW RATE

CROSS REFERENCE TO RELATED APPLICATIONS

The present application is US national stage of international application PCT/EP2020/051497, which had an international filing date of Jan. 22, 2020, and which was published on Aug. 6, 2020. The application claims the benefit of U.S. 62/800,168, filed on Feb. 1, 2019. The content of these prior applications is hereby incorporated by reference in its entirety.

FIELD OF THE INVENTION

The invention is directed at separating a gas stream having varying composition or flow rate and comprising a first gas component and a more slowly permeating second gas component, by a membrane process to provide a product gas stream enriched in the second gas component having essentially constant composition.

BACKGROUND OF THE INVENTION

Membrane processes for gas separation have found wide spread application as they require less process chemicals, moving mechanical equipment and energy than gas separation process using gas liquefaction, absorption onto a solid or absorption into a liquid. Prior art membrane processes are very efficient for separating gas streams having essentially constant composition and flow rate, but have certain disadvantages for separating gas streams having varying composition or flow rate. When a membrane process is used for providing a product gas enriched in the slower permeating gas component having a content of faster permeating gas component below a specified limit, as in producing biomethane (also called renewable natural gas) from biogas or pipeline grade natural gas from raw natural gas, the membrane separation device has to be dimensioned to provide the required specification at the expected maximum gas flow rate and maximum content of faster permeating gas component. Otherwise, operating such a device with an increased gas flow rate or with a gas stream having a higher content of faster permeating gas component will lead to an increase in the concentration of the faster permeating gas in the product gas to above the specified limit. However, dimensioning a membrane separation device to the maximum possible gas flow rate, which only occurs occasionally, does not only lead to high investment costs for membranes, but also has the disadvantage that recovery of the slower permeating gas component will decrease when the device is operated at a gas flowrate lower than the maximum flow rate. For a biogas from an anaerobic digester or a landfill, where gas production rates change over the course of a day and up to the course of a season, this will be the case for most of the operating time.

WO 2014/075850 discloses a two stage two step membrane separation device comprising a feed stream separation unit, a retentate separation unit and a permeate separation unit, which uses control of permeate pressure in the retentate separation unit and of retentate pressure in the permeate separation unit to keep the composition of product streams constant when composition or flow rate of the gas feed varies. However, this concept cannot be applied in a one stage membrane separation device.

WO 2014/183977 discloses a one stage two step membrane separation device which uses control of permeate pressure in the first separation step based on flow rate or composition of the feed gas stream or composition of the product gas stream.

Regulating permeate pressure in reaction to changes in reaction to gas flow or composition requires operating the device at higher than necessary permeate pressure during most of the time in order to be able to act against increases in gas flow or content of faster permeating gas components.

Alternative concepts using splitting of streams in multi-step multi-stage processes to compensate for changes in feed gas flow or composition of biogas have been proposed in four Korean patents.

KR 1840337 B discloses a three step two stage process which uses a controller directing a varying fraction of the permeate obtained in the first stage first step to a second membrane stage depending on the methane content in the first step permeate. The retentate from the second stage first step is combined with the retentate from the first stage first step to provide the feed to the first stage second step.

KR 1840340 B discloses a three step two stage process which uses a first controller directing a varying fraction of the retentate obtained in the first stage second step to the first stage third step depending on the methane content in the feed stream, and a second controller directing a varying fraction of the second stage first step retentate to the second stage second step depending on the carbon dioxide content in this retentate, the second stage first step receiving permeate of the first stage second step as feed.

KR 1840343 B discloses the three step two stage process of KR 1840340 B without the first controller and without splitting the first stage second step retentate stream.

KR 1863058 discloses the three step two stage process of KR 1840340 B without the second controller and without splitting the second stage first step retentate stream.

All four processes require a device with at least five membrane units in two stages.

U.S. Pat. No. 6,197,090 discloses a two step single stage membrane separation process where a part of the first step permeate is recycled to the feed stream, the fraction being controlled based on the concentration of the faster permeating gas component in the first step permeate or to maintain constant pressure of the feed stream.

SUMMARY OF THE INVENTION

The inventors of the present invention have now found that variations in composition or flow rate of a gas stream can be compensated to provide a product gas enriched in a slower permeating gas component having essentially constant purity with regard to a faster permeating gas component without the need for varying pressures in the process by using a single stage three step arrangement of membrane units with recycle of the third step permeate to the feed stream and varying the fraction of the second step permeate recycled to the feed stream. Adjusting the fraction of the second step permeate recycled to the feed stream to maintain a target composition of the third step retentate can additionally compensate changes in membrane efficiency caused for example by membrane contamination, which may occur when liquid enters the membrane module or gas components condense on the membrane, or by blocking of fibers of a hollow fiber membrane module.

DETAILED DESCRIPTION OF THE INVENTION

Figure 1:
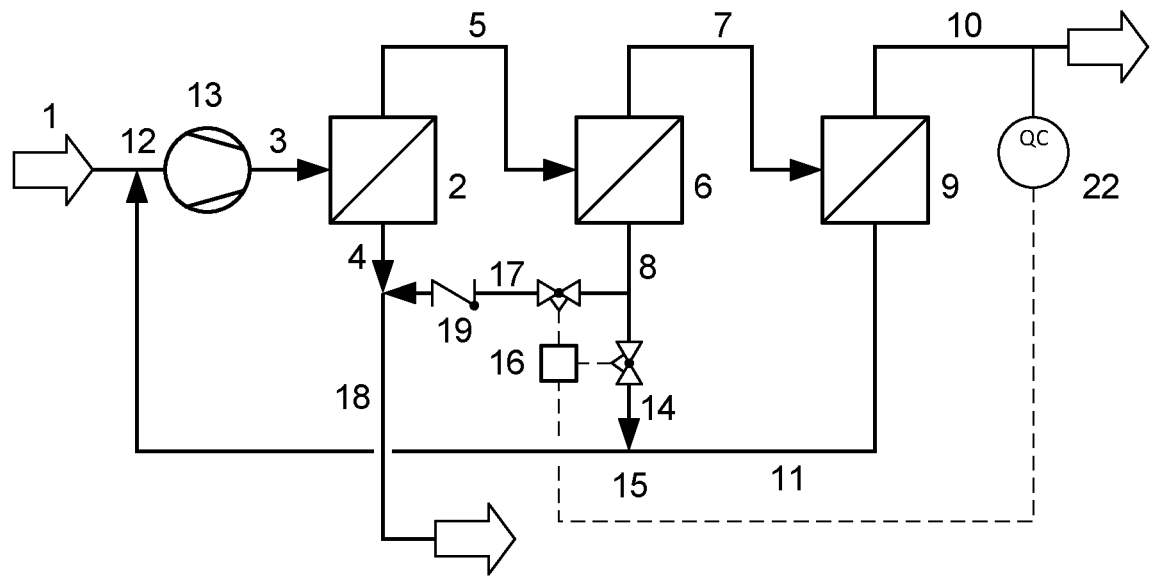
FIG. 1 shows an embodiment of the device and process of the invention where a gas analyzer (22) connected to control device (16) is used to control the fraction of the second permeate stream that is recycled in order to maintain a gas property of the third retentate stream.

The device of the invention is designed for separating a gas stream (1) which comprises a first gas component and a second gas component and which can have a varying composition or flow rate. The device of the invention comprises three membrane separation units and a gas compressor, as well as conduits connecting them and a control device which controls the splitting of a specific process stream.

The device of the invention comprises a first membrane separation unit (2) which receives the gas stream (1) through a feed conduit (3) and comprises a gas separation membrane which has higher permeance for the first gas component than for the second gas component. This first membrane separation unit (2) provides a first permeate stream and a first retentate stream. A first permeate conduit (4) is connected to the first membrane separation unit (2) to receive the first permeate stream and a first retentate conduit (5) is connected to the first membrane separation unit (2) to receive the first retentate stream.

The term permeate here refers to a gas mixture comprising the gas components of the gas mixture fed to the membrane separation unit which have passed the gas separation membrane due to a difference in partial pressure across the membrane. The term retentate refers to the gas mixture which remains after the gas components forming the permeate have passed the gas separation membrane. Since the gas separation membrane has higher permeance for the first gas component than for the second gas component, the permeate will be enriched in the first gas component and the retentate will be depleted in the first gas component compared to the gas mixture fed to the first membrane separation unit (2).

Permeance is defined as gas flow per time unit, area and differential pressure through a membrane and is usually determined in gas permeation units (GPU, $10^{-6}$ cm$^3$cm$^{-2}$s$^{-1}$ cm(Hg)$^{-1}$) based on volume flow. Permeance P in GPU for a particular membrane and gas component is determined from permeation experiments with the pure gas as $P=10^6*Q/(RT*\Delta p)$ with Q being the normalized gas flow through the membrane in cm$^3$/s at standard conditions, R being the gas constant, T being the temperature and $\Delta p$ being the pressure difference across the membrane in cm(Hg).

Pure gas selectivity S of a membrane for the first gas component over the second gas component is defined as $S=P_1/P_2$ with $P_1$ being the permeance for the first gas component and $P_2$ being the permeance for the second gas component.

Separation capacity of a membrane separation unit is defined as the product of the total membrane area of the membrane separation unit and the permeance of the membrane used in the membrane separation unit.

Suitable gas separation membranes are known from the prior art. Gas separation membranes containing a separation layer of a glassy polymer, i.e. a polymer having a glass transition point at a temperature above the operating temperature of the membrane separation unit, are preferred because they will usually provide higher selectivity than membranes with a separation layer of a different polymer type. The glassy polymer may be a polyetherimide, a polycarbonate, a polyamide, a polybenzoxazole, a polybenzimidazole, a polysulfone or a polyimide and the gas separation membrane preferably comprises at least 80% by weight of a polyimide or a mixture of polyimides.

In a preferred embodiment, the gas separation membrane of the first membrane separation unit comprises at least 50% by weight of a polyimide prepared by reacting a dianhydride selected from 3,4,3',4'-benzophenonetetracarboxylic dianhydride, 1,2,4,5-benzenetetracarboxylic dianhydride, 3,4,3', 4'-biphenyltetracarboxylic dianhydride, oxydiphthalic dianhydride, sulphonyldiphthalic dianhydride, 1,1,1,3,3,3-hexafluoro-2,2-propylidenediphthalic dianhydride and mixtures thereof with a diisocyanate selected from 2,4-tolylene diisocyanate, 2,6-tolylene diisocyanate, 4,4'-methylenediphenyl diisocyanate, 2,4,6-trimethyl-1,3-phenylene diisocyanate, 2,3,5,6-tetramethyl-1,4-phenylene diisocyanate and mixtures thereof. The dianhydride is preferably 3,4,3',4'-benzophenonetetracarboxylic dianhydride or a mixture of 3,4,3',4'-benzophenonetetracarboxylic dianhydride and 1,2,4,5-benzenetetracarboxylic dianhydride. The diisocyanate is preferably a mixture of 2,4-tolylene diisocyanate and 2,6-tolylene diisocyanate or a mixture of 2,4-tolylene diisocyanate, 2,6-tolylene diisocyanate and 4,4'-methylenediphenyl diisocyanate. Suitable polyimides of this type are commercially available from Evonik Fibres GmbH under the trade name P84® type 70, which has CAS number 9046-51-9 and is a polyimide prepared from 3,4,3',4'-benzophenonetetracarboxylic dianhydride and a mixture of 64 mol % 2,4-tolylene diisocyanate, 16 mol % 2,6-tolylene diisocyanate and 20 mol % 4,4'-methylenediphenyl diisocyanate, and under the trade name P84® HT, which has CAS number 134119-41-8 and is a polyimide prepared from a mixture of 60 mol % 3,4,3',4'-benzophenonetetracarboxylic dianhydride and 40 mol % 1,2,4,5-benzenetetracarboxylic dianhydride and a mixture of 80 mol % 2,4-tolylene diisocyanate and 20 mol % 2,6-tolylene diisocyanate. The gas separation membranes of this embodiment have preferably been heat treated in an inert atmosphere as described in WO 2014/202324 A1 to improve their long term stability in the process of the invention.

The gas separation membrane may be flat membrane or a hollow fiber membrane and is preferably an asymmetrical hollow fiber membrane comprising a dense polyimide layer on a porous support. The term "dense layer" here refers to a layer which comprises essentially no macropores extending through the layer and the term "porous support" here refers to a support material having macropores extending through the support. The asymmetrical hollow fiber membrane can be prepared by coating a porous hollow fiber with a polyimide to form a dense polyimide layer on the support.

In a preferred embodiment, the asymmetrical hollow fiber membrane is a membrane prepared in a phase inversion process by spinning with an annular two component spinning nozzle, passing a solution of a polyimide through the annular opening and a liquid containing a non-solvent for the polyimide through the central opening. This process provides an asymmetrical hollow fiber membrane with a dense layer on a porous support both consisting of the same polyimide.

The gas separation membrane preferably comprises a dense separation layer of a glassy polymer coated with an additional dense layer of a rubbery polymer, the rubbery polymer having a higher gas permeability than the glassy polymer. The preferred gas separation membranes comprising a polyimide separation layer are preferably coated with a polydimethylsiloxane elastomer.

The device of the invention further comprises a second membrane separation unit (6) which is connected to the first retentate conduit (5) to receive the first retentate stream as feed. This second membrane separation unit (6) comprises a gas separation membrane having higher permeance for the first gas component than for the second gas component and provides a second retentate stream and a second permeate stream. A second retentate conduit (7) is connected to the second membrane separation unit (6) to receive the second retentate stream and a second permeate conduit (8) is connected to the second membrane separation unit (6) to receive the second permeate stream.

The device of the invention further comprises a third membrane separation unit (9) which is connected to the second retentate conduit (7) to receive the second retentate stream as feed. This third membrane separation unit (9) comprises a gas separation membrane having higher permeance for the first gas component than for the second gas component and provides a third retentate stream and a third permeate stream. A product conduit (10) is connected to the third membrane separation unit (9) to receive the third retentate stream.

Each of the three membrane separation units may comprise several membrane modules arranged in parallel and may also comprise several membrane modules arranged in series. When the gas separation membrane is a flat membrane, the membrane separation unit preferably comprises one or several spiral wound membrane modules containing the flat membranes. When the gas separation membrane is a hollow fiber membrane, the membrane separation unit preferably comprises one or several membrane modules, each containing a bundle of hollow fiber membranes. When a membrane separation unit comprises membrane modules arranged in series, the retentate provided by a membrane module is passed as feed to the membrane module subsequent in the series of membrane modules, the last membrane module of the series providing the retentate of the membrane separation unit, and the permeates of all membrane modules within a series are combined to provide the permeate of the membrane separation unit. When a membrane separation unit comprises several hollow fiber membrane modules arranged in series, the membrane modules are preferably removable membrane cartridges arranged in series as a chain of cartridges in a common pressure vessel and connected to each other by a central permeate collecting tube, as described in detail in WO 2016/198450 A1.

The three membrane separation units may comprise the same type of gas separation membrane. In this case, the second and the third membrane separation unit comprises the same type of gas separation membrane as described further above for the first membrane separation unit.

In a preferred embodiment, the first membrane separation unit (2) comprises gas separation membranes which have a higher pure gas selectivity at 20° C. for the first gas component over the second gas component than the gas separation membranes comprised by the second membrane separation unit (6), and which have a lower permeance at 20° C. for the first gas component than the gas separation membranes comprised by the second membrane separation unit (6). The third membrane separation unit (9) may then comprise the same gas separation membranes as the second membrane separation unit (6) or different gas separation membranes. Preferably, the gas separation membranes of the first membrane separation unit (2) have a pure gas selectivity at 20° C. for carbon dioxide over methane which is from 1.05 to 2 times the pure gas selectivity of the gas separation membranes comprised by the second membrane separation unit (6), determined at the same temperature and for the same gas components. When the first membrane separation unit (2) comprises the preferred polyimide gas separation membrane prepared from a dianhydride and a diisocyanate as described further above, the second membrane separation unit (6) preferably comprises a gas separation membrane which comprises at least 50% by weight of a block copolyimide as described in WO 2015/091122 on page 6, line 20 to page 16, line 4. The block copolyimide preferably comprises at least 90% by weight of polyimide blocks having a block length of from 5 to 1000, preferably from 5 to 200.

In another preferred embodiment, which may be combined with the preceding embodiment, the second membrane separation unit (6) comprises gas separation membranes which have a higher pure gas selectivity at 20° C. for the first gas component over the second gas component than the gas separation membranes comprised by said third membrane separation unit (9), and which have a lower permeance at 20° C. for said first gas component than the gas separation membranes comprised by said third membrane separation unit (9). Preferably, the gas separation membranes of the second membrane separation unit (6) have a pure gas selectivity at 20° C. for carbon dioxide over methane which is from 1.05 to 3 times the pure gas selectivity of the gas separation membranes comprised by the third membrane separation unit (9), determined at the same temperature and for the same gas components. The third membrane separation unit preferably also comprises a gas separation membrane which comprises at least 50% by weight of a block copolyimide as described in WO 2015/091122 on page 6, line 20 to page 16, line 4. The higher permeance of the membrane compared to the membrane used in the second membrane separation unit can be provided by selecting different polymer blocks or using different block lengths.

The device of the invention also comprises a first recycle conduit (11) which is connected to the third membrane separation unit (9) to receive the third permeate stream, and is connected to a first recycle feed point (12) on the feed conduit (3) for recycling the third permeate stream.

The device of the invention further comprises a gas compressor (13) which is arranged in the feed conduit (3) between the first recycle feed point (12) and the first membrane separation unit (2) or is arranged in the first recycle conduit (11). The gas compressor (13) is placed between the first recycle feed point (12) and the first membrane separation unit (2) when the gas stream (1) to be separated is received at ambient pressure or at slightly above ambient pressure and needs to be compressed to the pressure used for operating first membrane separation unit (2). When the gas stream (1) to be separated is received at a pressure that is sufficient for operating the first membrane separation unit (2), only gas to be recycled needs to be compressed and the gas compressor (13) can be placed in the first recycle conduit (11). Any gas compressor compatible with the components of the gas stream (1) may be used, such as a turbo compressor, a piston compressor or preferably a screw compressor. The screw compressor may be a dry running compressor or a fluid-cooled compressor cooled with water or oil. When an oil cooled compressor is used, the device preferably also contains a droplet separator between the gas compressor (13) and the first membrane separation unit (2) to prevent oil droplets from entering the first membrane separation unit (2). Preferably, a cooler is placed in the feed conduit (3) between gas compressor (13) and the first membrane separation unit (2) to cool the compressed gas before it enters the first membrane separation unit (2). The cooler may also comprise a condenser for condensing moisture or other condensable components and an additional heater may be placed between this condenser and the first membrane separation unit (2) in order to prevent condensation of condensable gas components on a gas separation membrane of the membrane separation units.

The device of the invention also comprises a second recycle conduit (14) which is connected to the second permeate conduit (8) to receive all or a fraction of the second permeate stream, and is connected to a second recycle feed point (15) on the feed conduit (3) or on the first recycle conduit (11) for recycling the fraction of the second permeate stream which it receives. The second recycle feed point (15) is located upstream of the gas compressor (13) which allows for recycling all or a fraction of the second permeate stream without extra equipment. A control device (16) is configured to control which fraction of the second permeate stream is passed to the second recycle conduit (14). The remainder of the second permeate stream is passed to a discharge conduit (17). The control device may effect splitting of the second permeate stream into a fraction fed to the second recycle conduit (14) and the remaining fraction fed to the discharge conduit (17) by operating a three way split valve or by operating two separate valves, a first valve in the second recycle conduit (14) and a second valve in the discharge conduit (17). Control valves are preferred over switching valves for this purpose in order to prevent fluctuations of pressure and flow rates when operating the device.

The control device (16) may be configured to provide feed-forward control of the fraction of the second permeate stream which is recycled through the second recycle conduit (14). This may be achieved by providing a flow meter and/or a gas analyzer on the feed conduit (3) upstream of the first recycle feed point (12) for determining the flow rate and/or the composition of the gas stream (1) to be separated, connecting the control device (16) to the flow meter and/or gas analyzer and configuring the control device (16) to set control valves for splitting the second permeate stream into a fraction fed to the second recycle conduit (14) and the remaining fraction fed to the discharge conduit (17). In this embodiment, additional flow meters in the second permeate conduit (8), the second recycle conduit (14), the discharge conduit (17) or any combination thereof may be used, which are connected to control device (16) in order to set a desired split rate for the second permeate stream depending on the flow rate and/or the composition of the gas stream (1) to be separated.

In an alternative and preferred embodiment, control device (16) is configured to provide feed-back control of the fraction of the second permeate stream which is recycled through the second recycle conduit (14). For this purpose, a gas analyzer (22) is connected to the product conduit (10) for determining a gas property of the third retentate stream, the gas analyzer (22) is connected to control device (16) to transmit information on the gas property, and control device (16) is configured to maintain the gas property at a target value by controlling the fraction of the second permeate stream being passed to the second recycle conduit (14), preferably by control valves. The gas property determined by the gas analyzer (22) is preferably the content of the first gas component, the content of the second gas component or the calorific value.

In a preferred embodiment, the first permeate conduit (4) and the discharge conduit (17) are connected to a joint discharge conduit (18), which will then receive both the first permeate stream and the part of the second permeate stream which is not recycled. This is advantageous when the permeate streams leaving the device contain a gas component that shall be monitored or that requires further treatment of the permeate streams, such as for example removal of organic components with a thermal oxidizer. When there is a connection between the first permeate conduit (4) and the discharge conduit (17) by joint discharge conduit (18), a check valve (19) is preferably arranged in product discharge conduit (17) to prevent any passage of the first permeate stream from the first permeate conduit (4) to the second recycle conduit (14).

In another preferred embodiment, the device of the invention additionally comprises a first vacuum pump (20) arranged in the first recycle conduit (11), which provides subatmospheric pressure on the permeate side of the third membrane separation unit (9). This allows operating the third membrane separation unit (9) with a higher pressure difference across the gas separation membrane, which reduces the membrane area needed in the third membrane separation unit (9). First vacuum pump (20) may be a positive displacement pump or a blower. The additional first vacuum pump (20) is preferably placed upstream of the second recycle feed point (15) to ensure that the pressure in discharge conduit (17) cannot drop to below ambient pressure.

In another preferred embodiment, which may be combined with the preceding embodiment, the device of the invention additionally comprises a second vacuum pump (21) arranged in the second permeate conduit (8) upstream of discharge conduit (17), which provides subatmospheric pressure on the permeate side of the second membrane separation unit (6). This allows operating the second membrane separation unit (6) with a higher pressure difference across the gas separation membrane, which reduces the membrane area needed in the second membrane separation unit (6).

In another preferred embodiment, the third membrane separation unit (9) comprises at least two membrane modules (9a, 9b) arranged in parallel and at least one shut-off valve (23) for taking one or more membrane modules (9b) off stream. In this embodiment, a membrane module (9b) to be taken off stream preferably comprises a shut-off valve (23) in the feed conduit to the membrane module (9b). A check valve may be placed in the conduit receiving retentate from membrane modules (9b) to be taken off stream, in order to prevent back flow from the product conduit (10) through the gas separation membrane of membrane module (9b) to the first recycle conduit (11). In a preferred alternative, the same result is achieved with a second shut-off valve in the conduit receiving permeate from membrane modules (9b) to be taken off stream. When the device of the invention comprises membrane modules (9b) to be taken off stream, the device preferably comprises a flow meter on the feed conduit (3) upstream of the first recycle feed point (12) for determining the flow rate of the gas stream (1) to be separated, and an additional control device configured to open or close shut-off valves (23) for taking membrane modules (9b) on or off stream depending on the flow rate of the gas stream (1) to be separated.

The separation capacity of the membrane separation units of the device of the invention is preferably chosen to provide a specified target composition of the third retentate stream and a specified recovery rate for recovering the second gas component with the third retentate stream at the routine load of the device, which is the flow rate of gas stream (1) for which the device is designed (otherwise also referred to as the nameplate capacity), when operating the device with recycling from 80% to 100% of the second permeate stream to the second recycle feed point (15). Preferably, the separation capacity of the membrane separation units is chosen to a provide a particular maximum load higher than the routine load when operating the device without any recycling of the second permeate stream, providing essentially the same target composition of the third retentate stream, albeit with a lower recovery rate. Suitable separation capacities can be determined with process simulation software, carrying out simulation of the membrane separation based on experimentally determined values for permeance and selectivity of the membranes.

The process of the invention for separating a gas stream (1) comprising a first gas component and a second gas component is carried out in a device of the invention. The process of the invention comprises feeding the gas stream (1) to feed line (3) of a device of the invention, preferably upstream of the gas compressor (13), withdrawing the third retentate stream from product conduit (10) as a product gas stream enriched in the second gas component, and withdrawing an off-gas stream enriched in the first gas component. The off-gas stream is either withdrawn by withdrawing the first permeate stream from first permeate conduit (4) or, if a joint discharge conduit (18) is present, by withdrawing the stream resulting from combining the first permeate stream with the remainder of the second permeate stream passed to discharge conduit (17) from joint discharge conduit (18).

The process of the invention is preferably carried out with a gas stream (1) comprising carbon dioxide as the first gas component and methane as the second gas component. The gas stream (1) may then be a natural gas or a biogas, preferably with a combined content of methane and carbon dioxide of more than 90% by volume, i.e. comprising less than 10% by volume of components other than methane and carbon dioxide. The gas stream (1) is preferably a biogas from a landfill, a waste water treatment or an anaerobic digester.

In the process of the invention, the fraction of the second permeate stream being passed to the second recycle conduit (14) is preferably adjusted when the flow rate of the gas stream (1) changes or when the composition of the gas stream (1) changes or in both cases. Preferably, the fraction of the second permeate stream which is passed to the second recycle conduit (14) is increased when the flow rate of gas stream (1) decreases and is decreased when the flow rate of gas stream (1) increases. Alternatively or in combination, the fraction of the second permeate stream which is passed to the second recycle conduit (14) is increased when the fraction of the first gas component in gas stream (1) decreases and is decreased when the fraction of the first gas component in gas (1) stream increases. The fraction of the second permeate stream which is passed to the second recycle conduit (14) may be varied from a fraction of 0, which means that all of the second permeate stream is passed to the discharge conduit (17), up to a fraction of 1, which means that all of the second permeate stream is passed to the second recycle conduit (14), with any value between 0 and 1 being possible.

When the convention is applied, that the minimum number of membrane units, which the permeate product of a membrane separation process has to pass, is counted as membrane stages and the minimum numbers of membrane units, which the retentate product of a membrane separation process passes providing permeates of different composition, is counted as membrane steps, the process of the invention with a recycle fraction for the second permeate stream of between 0 and 1 is a single stage three step membrane separation process. However, for a recycle fraction of 0 the process effectively becomes a single stage two step membrane separation process with a large membrane area in the first step, because the permeates from the first and second membrane separation unit are combined, whereas for a recycle fraction of 1 the process effectively becomes a single stage two step membrane separation process with a large membrane area in the second step, because the permeates from the second and the third membrane separation unit are combined.

In a preferred embodiment of the process of the invention, a gas property of the third retentate stream is monitored by an analyzer (22), and the fraction of the second permeate stream being passed to the second recycle conduit (14) is controlled to maintain the gas property essentially constant. The gas property monitored by the analyzer (22) is preferably the content of the first gas component in the third retentate stream or the content of the second gas component in the third retentate stream or the calorific value of the third retentate stream. The content of the first or the second gas component is preferably kept constant to deviate less than 0.5% by volume from the target value and the calorific value is preferably kept constant to deviate less than 2% from the target value.

In another preferred embodiment of the process of the invention, which can be combined with the preceding preferred embodiment, a device of the invention is used where the third membrane separation unit (9) comprises a multitude of membrane modules arranged in parallel which can be taken off stream separately, and membrane modules of the third membrane separation unit (9) are taken off stream when the flow rate of the gas stream (1) decreases. Preferably, all membrane modules are on stream when the process is operated at the maximum flow rate of gas stream (1). Membrane modules may be taken off stream based on measuring the actual flow rate of the gas stream (1). Alternatively, membrane modules may be taken off stream when the concentration of carbon dioxide in the third retentate stream falls below a preset first threshold value and may be taken back on stream when the concentration of carbon dioxide in the third retentate stream increases to a value higher than a preset second threshold value.

EXAMPLES

Example 1

Separation of biogas from a landfill was calculated with a process simulation software for membrane separation modules having a pure gas selectivity of carbon dioxide over methane of about 55. Separation of 1260 Nm³/h of a biogas containing 58.7 vol-% methane, 40.0 vol-% carbon dioxide, 1.0 vol-% nitrogen and 0.3 vol-% oxygen was calculated for a three stage membrane separation in a device as shown in FIG. 1, with 21 membrane modules in the first membrane separation unit (2), 22 membrane modules in the second membrane separation unit (6) and 95 membrane modules in the third membrane separation unit (9).

The feed to the first membrane separation unit (2) is compressed to 13.1 bar and all three membrane separation units are operated with a pressure of 1.03 bar at the permeate side. Recycling 84% of the second permeate stream to second recycle feed point (15) and combining the remaining 16% with the first permeate stream provides 742 Nm³/h of a third retentate stream containing 97.0 vol-% methane, 1.1 vol-% carbon dioxide, 1.6 vol-% nitrogen and 0.3 vol-% oxygen. The third retentate stream contains 97.3% of the methane contained in the biogas fed to the device and the process requires compressing 1712 Nm³/h of gas (36% double compression).

Methane content of the third retentate stream can be maintained at the same value for higher flow rates of biogas of up to 1400 Nm³/h by recycling less of the second permeate stream. Separation of 1400 Nm³/h of the same biogas without recycling any of the second permeate stream provides 804 Nm³/h of a third retentate stream containing 97.0 vol-% methane, 1.2 vol-% carbon dioxide, 1.6 vol-% nitrogen and 0.2 vol-% oxygen. The third retentate stream then contains 95.0% of the methane contained in the biogas fed to the device and the process requires compressing 1636 Nm³/h of gas (17% double compression).

Separating a reduced gas flow of 1000 Nm³/h of biogas and recycling all of the second permeate stream to second recycle feed point (15) provides 582 Nm³/h of a third retentate stream containing 97.7 vol-% methane, 0.4 vol-% carbon dioxide, 1.6 vol-% nitrogen and 0.2 vol-% oxygen. The third retentate stream contains 97.0% of the methane contained in the biogas fed to the device and the process requires compressing 1359 Nm³/h of gas (36% double compression).

Comparative Example 1

Figure 3:
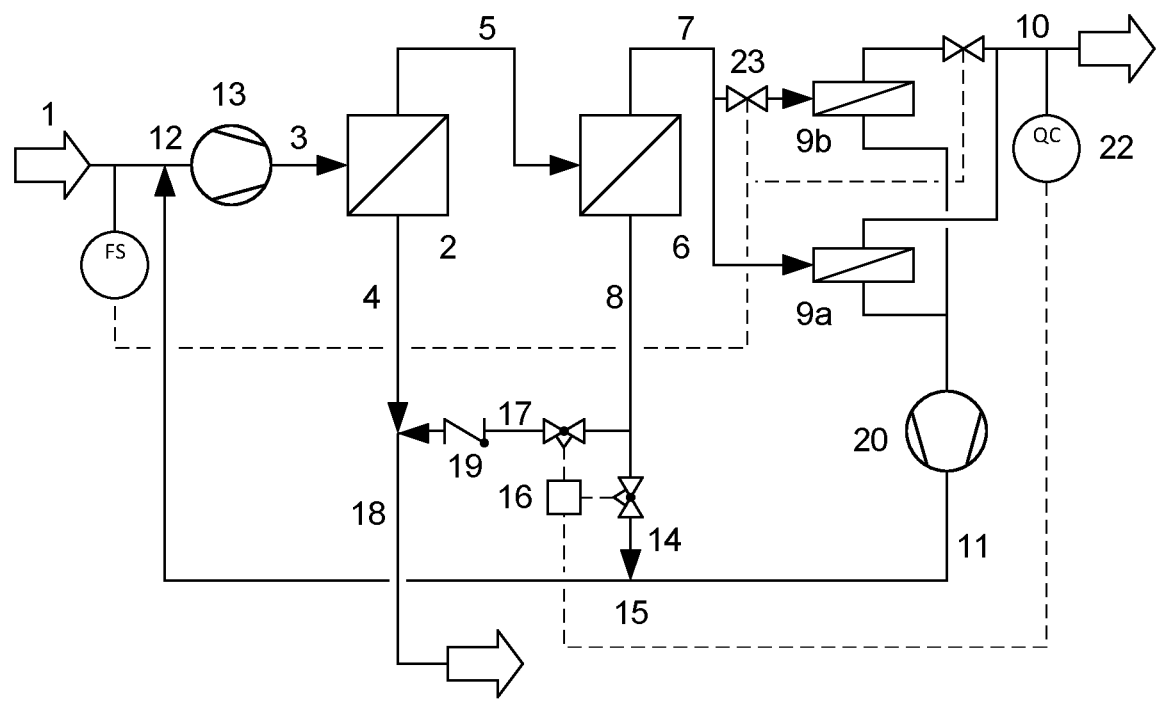
FIG. 3 shows an embodiment of the device and process of the invention where the third membrane separation unit (9) comprises two membrane modules (9a, 9b) and shut-off valves for taking membrane module (9b) off stream when the flow rate of gas stream (1) to be separated decreases below a threshold value.

The device shown in FIG. 3 of U.S. Pat. No. 6,197,090 operated without recycle from membrane separation unit 2a provides the same separation effect as the device of FIG. 1 of the invention operated without recycling any of the second permeate stream when membrane separation unit 2a contains the same number and type of membrane modules as the combined first and second membrane units of the inventive device (i.e. 43 membrane modules) and the membrane separation unit 2b contains the same number and type of membrane modules as the third membrane unit of the inventive device (i.e. 95 membrane modules). Therefore, at the maximum flow rate of 1400 Nm³/h and operated without a recycle stream G7, the device shown in FIG. 3 of U.S. Pat. No. 6,197,090 comparable to the device of example 1 provides a product stream G7 identical to the third retentate stream obtained with the device of the invention.

Simulating separation of the same biogas for the same device at the nameplate capacity flow rate of 1260 Nm³/h requires adjusting the recycle rate with recycle stream G7 to 28% in order to provide the same methane content of 97.0 vol-% methane in product stream G6. Product stream G6 is then obtained at a flow rate of 735 Nm³/h with a composition of 97.0 vol-% methane, 1.1 vol-% carbon dioxide, 1.6 vol-% nitrogen and 0.3 vol-% oxygen and contains 96.4% of the methane contained in the biogas fed to the device. The process then requires compressing 1718 Nm³/h of gas (36% double compression).

Separating a reduced gas flow of 1000 Nm³/h of biogas with the same device provides the same methane content of 97.0 vol-% methane at a recycle rate of recycle stream G7 of 64%. Product stream G6 is then obtained at a flow rate of 595 Nm³/h with a composition of 97.0 vol-% methane, 1.0 vol-% carbon dioxide, 1.6 vol-% nitrogen and 0.3 vol-% oxygen and contains 98.3% of the methane contained in the biogas fed to the device. The process then requires compressing 2032 Nm³/h of gas (103% double compression).

Example 1 and comparative example 1 demonstrate that the process of the invention provides better methane yields at nameplate capacity than the prior art process and requires much less compression energy when flow rate of the biogas drops below nameplate capacity with only a slight loss in methane yield.

Example 2

Figure 2:
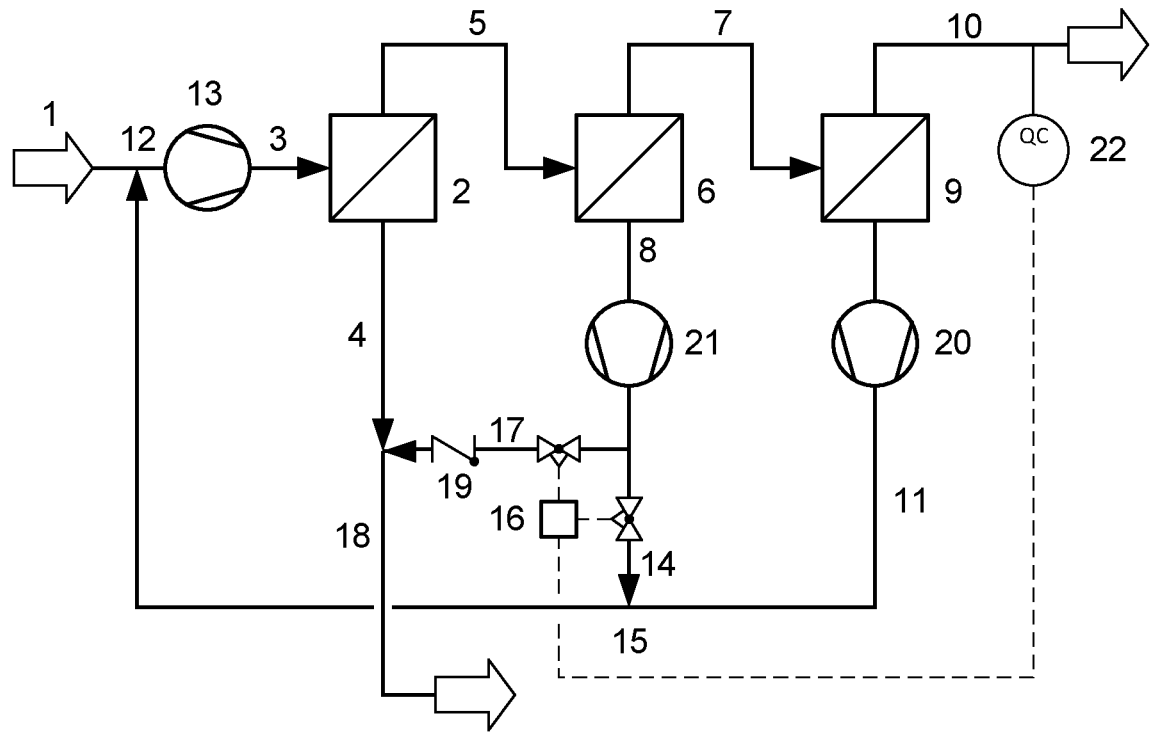
FIG. 2 shows an embodiment of the device and process of the invention where additional vacuum pumps (19, 20) are used to provide subatmospheric pressure on the permeate side of the second membrane separation unit (6) and the third membrane separation unit (9).

Separation of biogas from a landfill was calculated with a process simulation software for separation with a device as shown in FIG. 2, but lacking the second vacuum pump (21). Calculations were carried out for three different membrane types used in the three membrane separation units, a membrane type A having a pure gas selectivity of carbon dioxide over methane of 56 used in the first membrane separation unit (2), a membrane type B having a pure gas selectivity of carbon dioxide over methane of 50 and a permeance for carbon dioxide 2 times that of membrane type A used in the second membrane separation unit (6), and a membrane type C having a pure gas selectivity of carbon dioxide over methane of 25 and a permeance for carbon dioxide 4 times that of membrane type A used in the third membrane separation unit (9). The first membrane separation unit (2), the second membrane separation unit (6) and the third membrane separation unit (9) have total membrane areas in a ratio of 2:1:1. The feed to the first membrane separation unit (2) is compressed to 13.5 bar. The first and the second membrane separation unit are operated with a pressure of 1.0 bar at the permeate side and the third membrane separation unit is operated with a pressure of 0.6 bar at the permeate side generated by the first vacuum pump (20).

Separation of 1000 Nm³/h (nameplate capacity) of the same biogas as in example 1 with complete recycle of the second permeate stream to second recycle feed point (15) provides 591 Nm³/h of a third retentate stream containing 97.1 vol-% methane, 0.9 vol-% carbon dioxide, 1.6 vol-% nitrogen and 0.3 vol-% oxygen. The third retentate stream contains 97.7% of the methane contained in the biogas fed to the device and the process requires compressing 1455 Nm³/h of gas (46% double compression).

The same device when operated at maximum capacity of a biogas feed of 1145 Nm³/h with no recycle of the second permeate stream to second recycle feed point (15) provides 641 Nm³/h of a third retentate stream containing 97.2 vol-% methane, 1.0 vol-% carbon dioxide, 1.6 vol-% nitrogen and 0.2 vol-% oxygen. The third retentate stream then contains 92.8% of the methane contained in the biogas fed to the device and the process requires compressing 1370 Nm³/h of gas (20% double compression). Methane content of the third retentate stream can be maintained at a constant value for any biogas flow rate between nameplate capacity and maximum capacity by adjusting the fraction of the second permeate stream recycled to second recycle feed point (15).

Example 3

The calculation of example 2 was repeated with the difference that membrane type C was used in the second membrane separation unit (6) and the total membrane areas of the first membrane separation unit (2), the second membrane separation unit (6) and the third membrane separation unit (9) had a ratio of 2:0.6:1.

Separation of 1000 Nm$^3$/h (nameplate capacity) with complete recycle of the second permeate stream to second recycle feed point (15) then provides 589 Nm$^3$/h of a third retentate stream containing 97.3 vol-% methane, 0.8 vol-% carbon dioxide, 1.6 vol-% nitrogen and 0.3 vol-% oxygen. The third retentate stream contains 97.7% of the methane contained in the biogas fed to the device and the process requires compressing 1518 Nm$^3$/h of gas (52% double compression).

Operating the device at a maximum capacity of 1200 Nm$^3$/h with no recycle of the second permeate stream to second recycle feed point (15) provides 626 Nm$^3$/h of a third retentate stream containing 97.3 vol-% methane, 0.7 vol-% carbon dioxide, 1.7 vol-% nitrogen and 0.2 vol-% oxygen. The third retentate stream then contains 86.6% of the methane contained in the biogas fed to the device and the process requires compressing 1411 Nm$^3$/h of gas (18% double compression).

Example 4

The calculation of example 2 was repeated with the difference that membrane type A was used in the second membrane separation unit (6) and the total membrane areas of the first membrane separation unit (2), the second membrane separation unit (6) and the third membrane separation unit (9) had a ratio of 2:2:1.

Separation of 1000 Nm$^3$/h (nameplate capacity) with complete recycle of the second permeate stream to second recycle feed point (15) then provides 591 Nm$^3$/h of a third retentate stream containing 97.2 vol-% methane, 0.9 vol-% carbon dioxide, 1.6 vol-% nitrogen and 0.3 vol-% oxygen. The third retentate stream contains 97.7% of the methane contained in the biogas fed to the device and the process requires compressing 1454 Nm$^3$/h of gas (45% double compression).

Operating the device at a maximum capacity of 1145 Nm$^3$/h with no recycle of the second permeate stream to second recycle feed point (15) provides 644 Nm$^3$/h of a third retentate stream containing 97.2 vol-% methane, 1.0 vol-% carbon dioxide, 1.6 vol-% nitrogen and 0.2 vol-% oxygen. The third retentate stream then contains 93.2% of the methane contained in the biogas fed to the device and the process requires compressing 1369 Nm$^3$/h of gas (20% double compression).

Comparing example 4 with examples 1 and 3 demonstrates that using a membrane in the third membrane separation unit (9) which has less carbon dioxide selectivity but higher permeance than the membrane used in the second membrane separation unit (6) provides better methane recovery at flow rates above nameplate capacity.

Comparing examples 2 and 3 with example 4 demonstrates that using a membrane in the second membrane separation unit (6) which has less carbon dioxide selectivity but higher permeance than the membrane used in the first membrane separation unit (2) allows operating the device with less total membrane area achieving the same product purity and methane recovery at nameplate capacity.

Example 5

The calculation of example 2 was repeated with the difference that the third membrane separation unit (9) of the device has additional membrane modules (9b) that can be taken off stream as shown in FIG. 3, the additional membrane modules (9b) providing an additional 50% of membrane area in the third membrane separation unit (9).

Operating the device at nameplate capacity with complete recycle of the second permeate stream to second recycle feed point (15) and the additional membrane modules (9b) taken off stream provides the same separation result as in example 2.

Operating the device at a maximum capacity of 1400 Nm$^3$/h with no recycle of the second permeate stream to second recycle feed point (15) and the additional membrane modules (9b) taken on stream provides 797 Nm$^3$/h of a third retentate stream containing 97.3 vol-% methane, 0.9 vol-% carbon dioxide, 1.6 vol-% nitrogen and 0.2 vol-% oxygen. The third retentate stream then contains 94.3% of the methane contained in the biogas fed to the device and the process requires compressing 1772 Nm$^3$/h of gas (27% double compression).

Comparing example 5 with example 2 demonstrates that a device with a third membrane separation unit containing parallel membrane modules of which a part can be taken on or off stream depending on the flow rate of the gas to be separated can provide the required product purity at higher maximum capacity and provides better methane recovery at flow rates above nameplate capacity.

LIST OF REFERENCE SIGNS

1 Gas stream to be separated
2 First membrane separation unit
3 Feed conduit
4 First permeate conduit
5 First retentate conduit
6 Second membrane separation unit
7 Second retentate conduit
8 Second permeate conduit
9 Third membrane separation unit
9a, 9b Membrane modules of third membrane separation unit (9)
10 Product conduit
11 First recycle conduit
12 First recycle feed point
13 Gas compressor
14 Second recycle conduit
15 Second recycle feed point
16 Control device
17 Discharge conduit
18 Joint discharge conduit
19 Check valve
20 First vacuum pump
21 Second vacuum pump
22 Gas analyzer
23 Shut-off valve

The invention claimed is:
1. A device for separating a gas stream, comprising a first gas component and
a second gas component, comprising:
(a) a first membrane separation unit receiving said gas stream through a feed conduit, said first membrane separation unit comprising a gas separation membrane having higher permeance for said first gas component than for said second gas component, providing a first permeate stream enriched in said first gas component and a first retentate stream;

(b) a first permeate conduit connected to said first membrane separation unit to receive said first permeate stream;

(c) a first retentate conduit connected to said first membrane separation unit to receive said first retentate stream;

(d) a second membrane separation unit, connected to said first retentate conduit to receive the first retentate stream as feed, said second membrane separation unit comprising a gas separation membrane having higher permeance for said first gas component than for said second gas component, providing a second retentate stream and a second permeate stream;

(e) a second retentate conduit connected to said second membrane separation unit to receive said second retentate stream;

(f) a second permeate conduit connected to said second membrane separation unit to receive said second permeate stream;

(g) a third membrane separation unit, connected to said second retentate conduit to receive the second retentate stream as feed, said third membrane separation unit comprising a gas separation membrane having higher permeance for said first gas component than for said second gas component, providing a third retentate stream and a third permeate stream;

(h) a product conduit connected to said third membrane separation unit to receive said third retentate stream;

(i) a first recycle conduit connected to said third membrane separation unit to receive said third permeate stream, and connected to a first recycle feedpoint on said feed conduit;

(j) a gas compressor arranged in said feed conduit between said first recycle feed point and said first membrane separation unit or arranged in said first recycle conduit;

(k) a second recycle conduit connected to a second recycle feed point on said feed conduit or on said first recycle conduit, said second recycle feed point being located upstream of said gas compressor and said second recycle conduit being connected to said second permeate conduit to receive all or a fraction of said second permeate stream; and (l) a control device controlling the fraction of said second permeate stream being passed to said second recycle conduit and passing the remainder of said second permeate stream to a discharge conduit;

wherein said first permeate conduit and said discharge conduit are connected to a joint discharge conduit; and wherein:

i) said first membrane separation unit comprises a gas separation membrane with:

a pure gas selectivity at 20° C. for the first gas component over the second gas component that is from 1.05 to 2 times higher than the pure gas selectivity of a gas separation membrane in the second membrane separation unit for said first gas component over said second gas component at the same temperature and for the same gas components;

a permeance at 20° C. for said first gas component that is lower than the permeance of a membrane in the second membrane separation unit;

ii) said second membrane separation unit comprises a gas separation membrane with:

a pure gas selectivity at 20° C. for the first gas component over the second gas component that is higher than the selectivity of a membrane in the third membrane separation unit for said first gas component over said second gas component; and a permeance at 20° C. for said first gas component that is lower than the permeance of a membrane in the third membrane separation unit.

2. The device of claim 1, wherein a check valve is arranged in said product discharge conduit preventing passage of the first permeate stream from said first permeate conduit to said second recycle conduit.

3. The device of claim 1, additionally comprising a first vacuum pump arranged in said first recycle conduit, providing subatmospheric pressure on the permeate side of said third membrane separation unit.

4. The device of claim 1, additionally comprising a second vacuum pump arranged in said second permeate conduit upstream of said discharge conduit, providing subatmospheric pressure on the permeate side of said second membrane separation unit.

5. The device of claim 2, additionally comprising:

a) a first vacuum pump arranged in said first recycle conduit, providing subatmospheric pressure on the permeate side of said third membrane separation unit;

b) a second vacuum pump arranged in said second permeate conduit upstream of said discharge conduit, providing subatmospheric pressure on the permeate side of said second membrane separation unit.

6. The device of claim 1, additionally comprising a gas analyzer connected to said product conduit for determining a gas property of said third retentate stream, said gas property being selected from the content of said first gas component, the content of said second gas component and the calorific value, said gas analyzer being connected to said control device to transmit information on said gas property and said control device being configured to maintain said gas property at a target value by controlling the fraction of said second permeate stream being passed to said second recycle conduit.

7. The device of claim 1, wherein said third membrane separation unit comprises at least two membrane modules arranged in parallel and at least one shut-off valve for taking a membrane module off stream.

* * * * *